United States Patent [19]

Ting

[11] Patent Number: 5,044,743

[45] Date of Patent: Sep. 3, 1991

[54] CORRECTIVE LENS SYSTEM

[75] Inventor: Albert C. Ting, Rancho Santa Margarita, Calif.

[73] Assignee: Allergan, Inc., Irvine, Calif.

[21] Appl. No.: 287,468

[22] Filed: Dec. 20, 1988

[51] Int. Cl.$^5$ .......................... G02C 7/12; G02C 7/04; G02B 5/30; A61F 2/16

[52] U.S. Cl. ..................... 351/163; 359/493; 359/494; 359/501; 351/49; 351/159; 351/161; 351/165; 351/168; 351/177; 623/5; 623/6

[58] Field of Search ................. 351/163, 164, 165, 49, 351/168, 160 R, 160 H, 161, 162, 159, 177; 350/399, 400, 407; 623/5, 6

[56] References Cited

U.S. PATENT DOCUMENTS

| | | | |
|---|---|---|---|
| 2,519,428 | 8/1950 | Birch-Field | 350/407 |
| 3,339,997 | 9/1967 | Wesley | 351/164 |
| 3,397,608 | 8/1968 | Ellis | 350/407 |
| 3,410,624 | 11/1968 | Schmidt | 350/407 |
| 3,474,255 | 10/1969 | White | 350/407 X |
| 3,520,592 | 7/1970 | Leib et al. | 350/407 |
| 3,867,020 | 2/1975 | Braunhut | 351/49 |
| 3,941,476 | 3/1976 | Stauffer | 350/407 X |
| 4,595,262 | 6/1986 | Ogle | 350/407 X |

FOREIGN PATENT DOCUMENTS 8704264  7/1987  PCT Int'l Appl. .

*Primary Examiner*—Scott J. Sugarman
*Attorney, Agent, or Firm*—Gordon L. Peterson; Loyal M. Hanson

[57] ABSTRACT

A corrective lens system with selectable optical characteristics includes a lens element for placement in the optical path of a human eye ahead of the retina of the eye and a polarizer element for placement in the optical path of the human eye ahead of the lens element. The polarizer element is configured to pass plane polarized light toward the lens element and the lens element has first and second regions with different optical characteristics, the first region being polarized and arranged to restrict the passage of plane polarized light having other than a given direction of polarization. The lens element may be an intraocular lens, a contact lens, or a corneal implant lens, and one embodiment includes a polarizer element mounted on a spectacles frame as a component of an ocular telescope utilized to treat macular degeneration so that when the spectacles are worn light is restricted from passing through the first region of the lens element.

26 Claims, 2 Drawing Sheets

CORRECTIVE LENS SYSTEM

BACKGROUND OF THE INVENTION

1. Technical Field

This invention relates generally to corrective lenses, and more particularly to a new and improved lens system having selectable optical characteristics.

2. Background Information

We sometimes use multi-segmented optical surfaces to correct or compensate for different vision disorders, tailoring the optical characteristic of each segment to a specific patient need. Thus, one lens can be used to compensate for more than just one disorder. Bifocal and trifocal spectacle lenses as well as multi-segmented contact lenses, corneal implant lenses, and intraocular lenses share this attribute and function.

The patient selects the optical characteristics desired. In order to select the desired optical characteristics of a bifocal lens, for example, the patient merely looks through the appropriate segment. But selecting the desired optical characteristics with other lenses is more complicated.

Consider, for example, a teledioptric lens system utilized to compensate for macular degeneration. Recall that macular degeneration affects the central retinal area known as the macula and it can lead to a gradual or sudden loss of vision to the level of 20/200 or less. It may affect only about one-quarter to four square millimeters of the central retinal area, thereby leaving 95%-99% of the retina unaffected Thus, near vision, for example, for reading and watching television can be lost while far vision remains intact.

Telescopic systems that increase the retinal image size of a given object have been used to compensate for such loss of near vision. Such a system is described in pending U.S patent application Ser. No. 141,482 and it may include an intraocular lens (IOL) or optical implant which replaces the natural lens, the implant having both a diverging central portion and a converging peripheral portion. The diverging portion operates in conjunction with spectacles configured as an ocular telescope that focuses images for near vision while the converging portion operates in the absence of the spectacles to provide far vision.

With such a system, the patient selects the desired optical characteristics by donning or removing the spectacles. In other words, the patient selects the diverging portion of the intraocular lens by using the spectacles and the converging portion by removing them. But utilizing the spectacles in this way to select the diverging portion only emphasizes the diverging portion instead of stopping light from passing through the converging portion, and this can impair the patient's vision. Similar problems may accompany use of multi-segmented contact and corneal implant lenses.

Thus, it is desirable to have some way of selecting only the desired segment or portion without also having light pass through the other segment or portion

SUMMARY OF THE INVENTION

The present invention solves the problems outlined above by utilizing a polarized lens element and a polarizer element At least one segment or portion of the lens element is polarized so that placing the polarizer element in the optical path ahead of the lens element limits the transmission of light as desired Generally, a lens system constructed according to a major aspect of the invention includes a lens element for placement in the optical path of a human eye ahead of the retina of the eye and a polarizer element for placement in the optical path of the human eye ahead of the lens element.

The polarizer element is configured to pass plane polarized light toward the lens element. The lens element has first and second regions such that the first region has different optical characteristics from the second region, and the first region of the lens element is polarized and arranged to restrict the passage of plane polarized light having other than a given direction of polarization.

According to another aspect of the present invention, the lens element may be configured as an intraocular lens, optical implant, contact lens, or corneal implant lens, and the polarizer element may be mounted on a spectacles frame. There, it passes plane polarized light so that it has a direction of polarization other than the given direction of polarization, preferably rotated ninety degrees from the given direction, so that passage of light through the first region of the lens element is substantially restricted.

According to yet another aspect of the invention, the optical implant is a component of an ocular telescopic lens system and the polarizer element is a component of multiple-element spectacles utilized with the optical implant in compensating for macular degeneration.

According to still another aspect of the invention, there is provided an ocular telescopic lens system that includes an optical implant having first and second lens portions, the second lens portion of which is a diverging lens portion, and multiple-element spectacles having anterior and posterior lenses arranged to converge light toward the diverging lens portion. At least one of the anterior and posterior lenses is configured to pass plane polarized light and the first lens portion of the optical implant is polarized and arranged to restrict the passage of plane polarized light having other than a given direction of polarization.

In that regard, there is provided an optical implant that includes an optic dimensioned and arranged to be retained in an eye in the optical path of the eye and fixation means attached to the optic for supporting the optic in the eye. The optic has first and second lens portions, the first lens portion having optical characteristics different from the second portion and the first portion being polarized and arranged to restrict the passage of plane polarized light having other than a given direction of polarization.

In line with the above, a method of treating macular degeneration according to the invention includes providing an optical implant having first and second lens portions, the second lens portion of which is a diverging lens portion and the first portion of which is polarized to restrict the passage of plane polarized light having other than a given direction of polarization. The method includes providing spectacles that are configured as an ocular telescope arranged to converge plane polarized light toward the diverging lens portion of the optical implant. Then, the optical implant is implanted in a patient and the spectacles are applied to the patient in order to converge plane polarized light that has other than the given direction of polarization toward the diverging lens portion of the optical implant lens.

Thus, a method according to the invention of selectively restricting passage of light through a lens includes (a) providing a lens element having first and second regions, the first region having optical characteristics different than the second region and the second regions, the first region having optical characteristics different than the second region and the first region being polarized and arranged to restrict the passage of plane polarized light having other than a given direction of polarization; (b) providing a polarizer element configured to pass plane polarized light toward the lens element; (c) supporting the lens element in a human eye in the optical path of the eye and the retina of the eye; and (d) placing the polarizer elemet in the optical path of the eye ahead of the lens element so that the polarizer element passes plane polarized light having other than the tiven direction of polarization.

The above mentioned and other objects and features of this invention and the manner of attaining them will become apparent, and the invention itself will be best understood, by reference to the following description taken in conjunction with the accompanying illustrative drawings.

DESCRIPTION OF THE PREFERRED EMBODIMENTS

Figure 1:
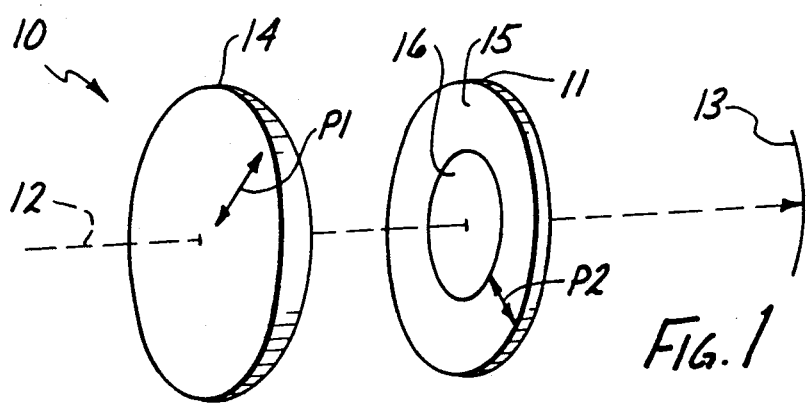
FIG. 1 is a diagrammatic view of a lens system constructed according to the invention.

Referring now to FIG. 1, there is shown a diagrammatic view of a lens system 10 constructed according to the invention. Generally, the lens system 10 includes a lens element 11 for placement in the optical path 12 of a human eye ahead of the retina 13 of the eye (between the retina and a field of view forward of the retina) and a polarizer element 14 for placement in the optical path 12 ahead of the lens element 11 (between the lens element 11 and the field of view).

The polarizer element 14 is fabricated from suitable known lens material configured according to known optical techniques to pass plane polarized light toward the lens element 11 that has a direction of polarization depicted by an arrow P1 in FIG. 1, lying in a plane transverse to the optical path 12.

The lens element 11 is fabricated from suitable known lens material to have first (outer) and second (inner) portions or segments or regions 15 and 16, the first region 15 having different optical characteristics from the second region 16. In addition, the first region 15 is polarized and arranged according to known techniques to restrict the passage of plane polarized light having other than a given direction of polarization depicted by an arrow P2 in FIG. 1 that also lies in a plane transverse to the optical path 12.

The direction of polarization of the polarizer element 14 (arrow P1) is other than the given direction of polarization of the first region of the lens element 11 (arrow P2). This arrangement operates to restrict passage through the lens element 11 of plane polarized light passing through the polarizer element 14. In FIG. 1, the arrow P1 is shown rotated ninety degrees from the arrow P2 in a preferred orientation that substantially restricts passage of the plane polarized light through region 15 of the lens element 11.

Figure 2:
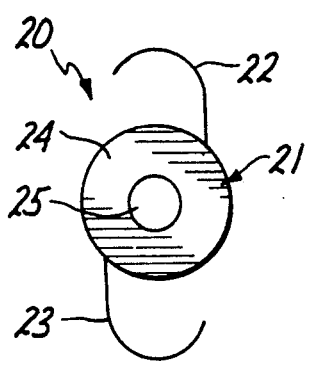
FIG. 2 is an front view of an optical implant utilized in one embodiment of the lens system.

According to one aspect of the invention, the lens element 11 takes the form of an intraocular lens 20 (FIG. 2). The lens 20 is generally similar to the intraocular lens 11 described in the U.S. patent application mentioned above, Ser. No. 141,482 filed Jan. 5, 1988, and that application is incorporated by reference for the details of the intraocular lens and ocular telescopic lens system it describes.

Thus, the intraocular lens 20 includes an optic 21 which is fabricated from a biocompatible material according to known techniques so that it is dimensioned and arranged to be retained in an eye in the optical path of the eye, i.e. transversing the optical path 12 illustrated in FIG. 1. One or more fixation members, such as first and second fixation member 22 and 23, are suitably attached to the optic 21 in a known manner to serve as fixation means for supporting the optic 21 in the eye.

The optic 21 includes a first region or converging portion 24 and a second region or diverging portion 25. The diverging portion 25 is a central portion of the optic 21 and the converging portion 24 is an annular portion of the optic 21 that circumscribes the diverging region 25. The converging portion 24 has different optical characteristics from the diverging portion 25 and is polarized as described above with reference to the lens element 11.

According to another aspect of the invention, the intraocular lens 20 is a component of an ocular telescopic lens system 30 (FIG. 3) utilized to compensate for macular degeneration. The system 30 is generally similar to the ocular telescopic lens system described in the above-referenced U.S. patent application. It includes the intraocular lens 20 supported in a human eye 31 and a multiple-element spectacle lens arrangement or ocular telescope or spectacle lens system 32 that cooperate as the ocular telescopic lens system 30 to increase the image size on a retina 33 of the eye 31. This enables many low-vision patients to read, watch television, and perform other tasks requiring near vision.

The spectacle lens system 32 includes an anterior lens 34 and a posterior lens 35. These are arranged coaxial with an optical path 36 of the eye 31 and relative to each other so that the lenses 34 and 35 converge light toward the diverging portion 25 of the intraocular lens 20. Light passes in sequence through the anterior lens 34, the posterior lens 35, and the intraocular lens 20 to the retina 33, the anterior and posterior lenses 34 and 35 combining to serve as an objective lens of the telescopic lens system they form with the diverging portion 25 of the intraocular lens 20.

The anterior and posterior lenses 34 and 35 are configured according to known lens design and fabrication techniques to achieve the converging optical characteristics desired. Additional lens elements may be employed with them for this purpose.

However, at least one of the anterior and posterior lenses 34 and 35 and any additional lens elements is configured to pass plane polarized light toward the intraocular lens 20 as described above with reference to the polarizer element 14 in FIG. 1. In the ocular telescopic lens system 30, the anterior lens 34 is so configured for this purpose. This is done so that the direction of polarization is rotated from the given direction of polarization of the converging portion 24 of the intraocular lens 20, preferably by ninety degrees as described above with reference to the lens element 11 in FIG. 1.

Figure 4:
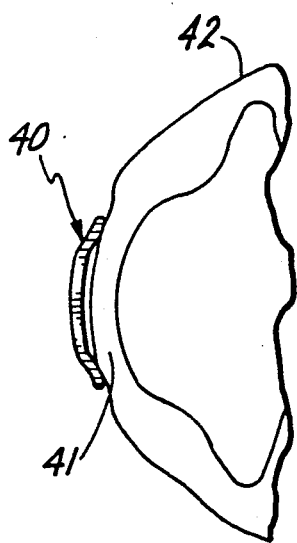
FIG. 4 is a cross sectional view of a contact lens utilized in another embodiment of the lens system.
Figure 5:
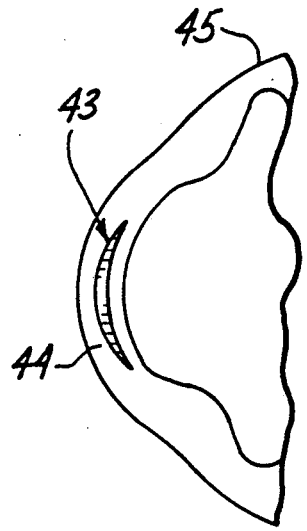
FIG. 5 is a cross sectional view of a corneal implant lens utilized in still another embodiment of the invention.

According to yet another aspect of the invention, the lens element 11 may take the form of a contact lens 40 supported conventionally ahead of a cornea 41 of an eye 42 as illustrated in FIG. 4, or a corneal implant lens 43 implanted partially or fully within a cornea 44 of an eye 45 as illustrated in FIG. 5 (including a corneal onlay lens). The contact lens 40 or corneal implant lens 43 include first and second regions having different optical characteristics as described above with reference to the lens element 11 in FIG. 1. They are fabricated from a suitable biocompatible material according to known techniques so that the first region is polarized as also described above. Of course, the first and second regions can be configured to have any of various shapes and orientations within the broader inventive concepts disclosed. In other words, the first region need not be in the form of an annular ring circumscribing the second region.

Figure 6:
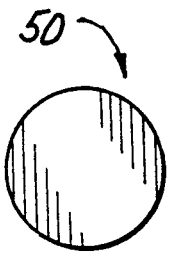
FIG. 6 is a front view of a polarizing element.
Figure 7:
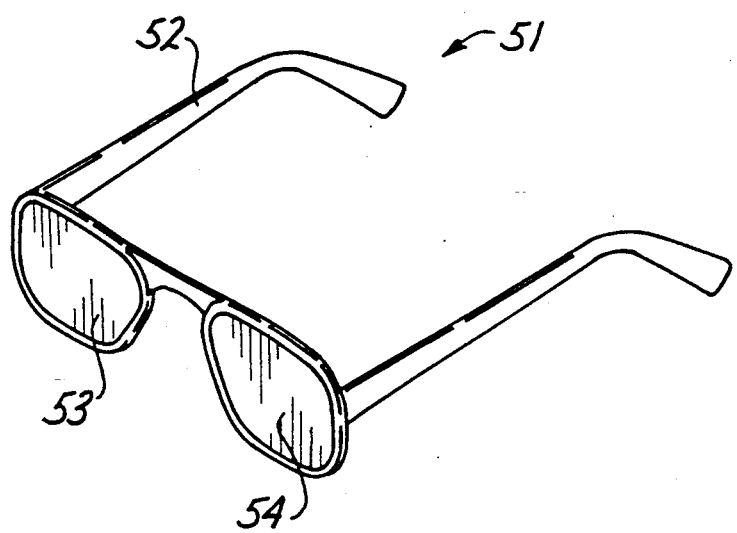
FIG. 7 is a perspective view of a pair of spectacles that has polarizing elements.

Considering now FIGS. 6 and 7, there is shown a polarizer element in the form of an optical element 50 (FIG. 6) and a pair of spectacles 51 that utilizes such a lens (FIG. 7). The spectacles 51 includes a frame 52 on which first and second polarizer elements 53 and 54 are mounted. Thus, a multiple-element arrangement is not required within the broader inventive concepts disclosed. Instead, the spectacles 51 can use just a single polarizer element for each eye.

Figure 8:
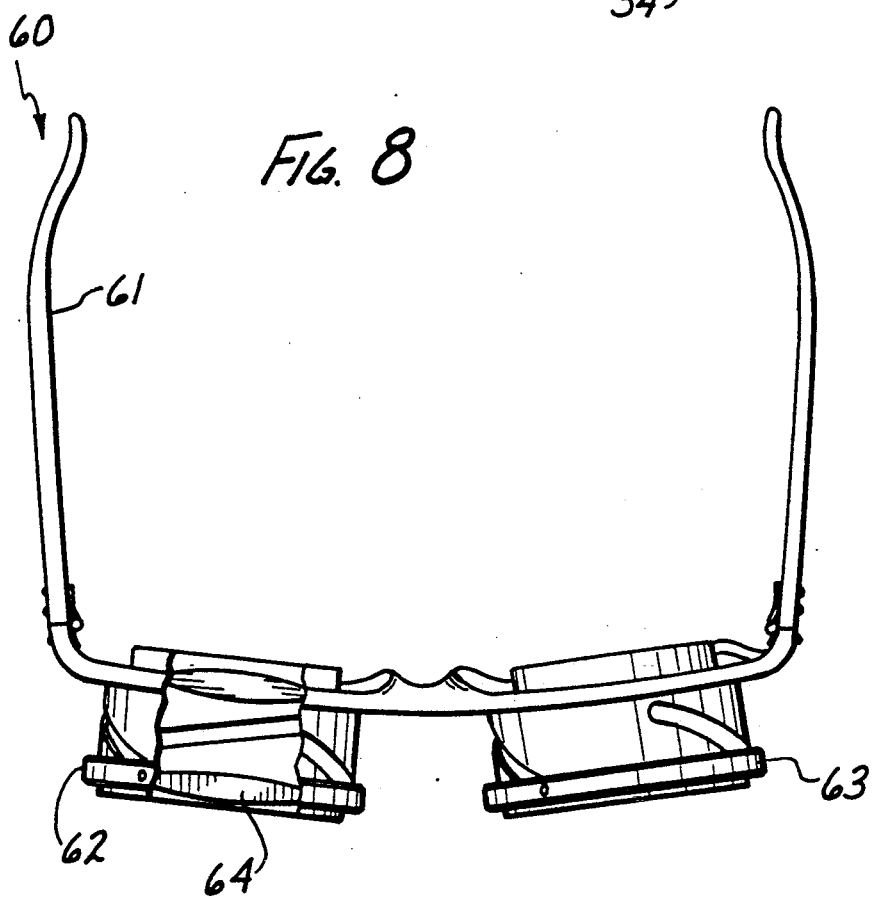
FIG. 8 is a partially cutaway plan view of multielement spectacles that include polarizing elements.

FIG. 8 is a partially cutaway plan view of a pair of multielement spectacles 60 that is generally similar to the multiple-element spectacles described in the above-referenced patent application. The pair of spectacles 60 is utilized as an ocular telescope in combination with an intraocular lens to compensate for macular degeneration and it includes a spectacles frame 61 on which two multiple lens arrangements 62 and 63 are mounted.

Figure 3:
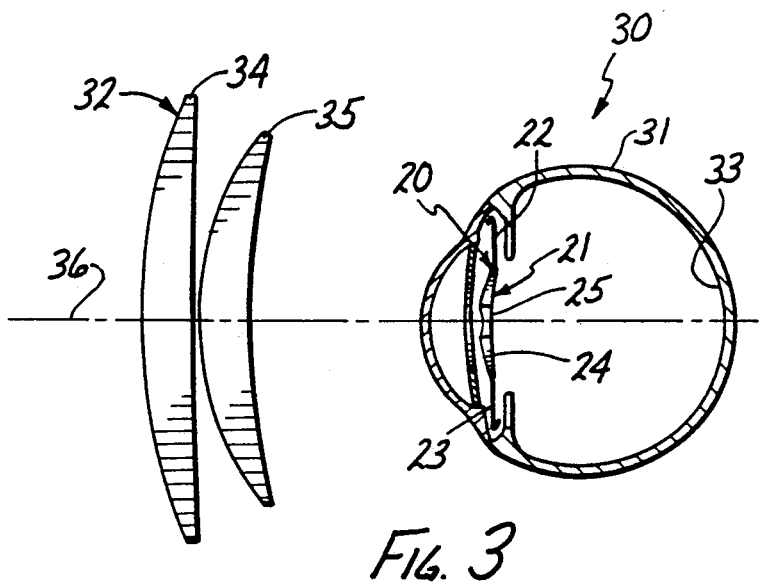
FIG. 3 is a diagrammatic view illustrating use of the intraocular lens with a pair of multielement spectacles.

At least one of the multiple lens arrangements 62 and 63 includes a polarizer element, however, like the multiple lens arrangement 32 described with reference to FIG. 3. Thus, the multiple lens arrangement 62 includes an anterior lens 64 that is configured to pass plane polarized light having a direction of polarization that is different than a given direction of polarization for a lens element with which the set of spectacles 60 are used, such as the intraocular lens 20.

When the patient dons the set of spectacles 60, plane polarized light is converged toward the diverging portion of the intraocular lens 20 while passage of the plane polarized light through the converging portion 24 is restricted to thereby limit peripheral distractions when the patient requires near vision. When the patient removes the set of spectacles 60, peripheral vision is restored.

Thus, a method of treating macular degeneration according to the invention includes the steps of (a) providing an intraocular lens having first and second lens portions, the second lens portion of which is a diverging lens portion and the first portion of which is polarized to restrict the passage of plane polarized light having other than a given direction of polarization; (b) providing spectacles that are configured as an ocular telescope arranged to converge plane polarized light toward the diverging lens portion of the intraocular lens; (c) implanting the intraocular lens in a patient; and (d) applying the spectacles to the patient in order to converge plane polarized light toward the diverging lens portion of the intraocular lens that has other than the given direction of polarization.

From a different perspective, a method of selectively restricting passage of light through a lens includes the steps of (a) providing a lens element having first and second regions, the first region having optical characteristics different from the second region and the first region being polarized and arranged to restrict the passage of plane polarized light having other than a given direction of polarization; (b) providing a polarizer element configured to pass plane polarized light toward the lens element; (c) supporting the lens element on or in a human eye in the optical path of the eye the retina of the eye; and (d) placing the polarizer element in the optical path of the eye ahead of the lens element so that it passes plane polarized light having other than the given direction of polarization.

The step of providing a polarizer element may include providing a polarizer element mounted on a spectacles frame as a component of an ocular telescope, and the step of providing a lens element may include providing a lens element configured as an intraocular lens, as a contact lens, or as a corneal implant lens.

Thus, this invention solves the problems of the prior art by utilizing a polarized lens element and a polarizing element to selectively control the transmission of light through multi-segmented optical surfaces.

Although an exemplary embodiment of the invention has been shown and described, many changes, modifications, and substitutions may be made by one having ordinary skill in the art without necessarily departing from the spirit and scope of the invention.

What is claimed is:

1. A lens system, comprising:
   a lens element dimensioned and arranged to be carried on or in an eye;
   a polarizer element for placement in the optical path of the eye ahead of the lens element;
   the polarizer element being configured to pass polarized light having a first direction of polarization toward the lens element;
   the lens element having first and second regions;
   the first region having different optical characteristics than the second region;
   the first region being polarized and arranged to restrict the passage of polarized light received from said polarizer element; and
   the second region passing polarized light received from said polarizer element.

2. A lens system as recited in claim 1, wherein:
   the polarizer element is mounted on a spectacles frame.

3. A lens system as recited in claim 2, wherein:
   the polarizer element is fixedly mounted on the spectacles frame.

4. A lens system as recited in claim 3, wherein:
   the polarizer element is fixedly mounted on the spectacles frame so that the polarized light from the poalrizer element has a direction of polarization rotated ninety degrees from the direction of polarization of the first region.

5. A lens system as recited in claim 1, wherein the lens element includes:

6. A lens system as recited in claim 5, wherein:
the second region of the lens element is a central portion of the optical implant; and
the first region of the lens element is an annular portion of the optical implant that circumscribes the second region.

7. A lens system as recited in claim 5, wherein:
the optical implant is a component of an ocular telescopic lens system.

8. A lens system as recited in claim 5, wherein:
the polarizer element is a component of multiple-element spectacles utilized in compensating for the effects of macular degeneration.

9. A lens system as recited in claim 1, wherein:
the lens element is a contact lens.

10. A lens system as recited in claim 1, wherein:
the lens element is a corneal implant lens.

11. A lens system as recited in claim 1, wherein:
the lens element is an intraocular lens.

12. A lens system as defined in claim 1 wherein the second region is unpolarized.

13. A lens system as defined in claim 1 wherein the first region circumscribes the second region.

14. A lens system as defined in claim 13 wherein the second region is a central region and is unpolarized, said lens system includes a spectacle frame, said polarizer element being carried by the spectacle frame.

15. An ocular telescopic lens system, comprising:
an optical implant having first and second lens portions, the second lens portion of which is a diverging lens portion; and
multiple-element spectacles having anterior and posterior lenses arranged to converge light toward the diverging lens portion;
at least one of the anterior and posterior lenses being configured to pass plane polarized light in a given direction; and
the first lens portion of the optical implant being polarized and arranged to restrict the passage of plane polarized light which is polarized in said given direction.

16. A method of treating macular degeneration, comprising:
providing an optical implant having first and second lens portions, the second lens portion of which is a diverging lens portion and the first portion of which is polarized to restrict the passage of plane polarized light having other than a given direction of polarization;
providing spectacles that are configured as an ocular telescope arranged to converge plane polarized light polarized in other than the given direction toward the diverging lens portion of the intraocular lens;
implanting the optical implant in a patient; and
applying the spectacles to the patient in order to converge plane polarized light that has other than the given direction of polarization toward the diverging lens portion of the optical implant.

17. A method of selectively restricting passage of light through a lens, comprising:
providing a lens element having first and second regions, the first region of having optical characteristics different than the second region and the first region being polarized and arranged to restrict the passage of plane polarized light having other than a given direction of polarization;
providing a polarizer element configured to pass plane polarized light toward the lens element;
supporting the lens element on a human eye in the optical path of the eye; and
placing the polarizer element in the optical path of the eye ahead of the lens element so that it passes plane polarized light having other than the given direction of polarization.

18. A method as recited in claim 17, wherein the step of providing a polarizer element includes:
providing a polarizer element mounted on a spectacles frame.

19. A method as recited in claim 18, wherein the step of providing a polarizer element includes:
providing a polarizer element mounted on a spectacles frame as a component of an ocular telescope.

20. A method as recited in claim 17, wherein the step of providing a lens element includes:
providing a lens element configured as an optical implant.

21. A method as recited in claim 17, wherein the step of providing a lens element includes:
providing a lens element configured as a contact lens.

22. A method as recited in claim 17, wherein the step of providing a lens element includes:
providing a lens element configured as a corneal implant lens.

23. A method as recited in claim 17, wherein the step of providing a lens element includes:
providing a lens element configured as an intraocular lens.

24. A lens system comprising:
a lens element dimensioned and arranged to be carried on or in an eye;
the lens element having first and second regions;
the first region having different optical characteristics than the second region;
the first region beign polarized and arranged to restrict the passage of light having a first direction of polarization;
the second region being capable of passing light having said first direction of polarization; and
a first lens arranged to converge light toward the lens element.

25. A lens system as defined in claim 24 including a spectacle frame carrying said first lens.

26. A lens system as defined in claim 25 including a second lens carried by said spectacle frame and cooperating with said first lens to converge light toward the lens element.

* * * * *